United States Patent
Yamauchi et al.

[11] Patent Number: 5,824,675
[45] Date of Patent: Oct. 20, 1998

[54] PREVENTIVE AND THERAPEUTIC AGENT FOR KIDNEY DISEASES

[75] Inventors: Yoichi Yamauchi, Komae; Takashi Nakagawa, Tokorozawa; Junichi Kawagoe, Tsurugashima, all of Japan

[73] Assignee: Kowa Co., Ltd., Nagoya, Japan

[21] Appl. No.: 817,639

[22] PCT Filed: Aug. 22, 1996

[86] PCT No.: PCT/JP96/02341

§ 371 Date: Apr. 28, 1997

§ 102(e) Date: Apr. 28, 1997

[87] PCT Pub. No.: WO97/07806

PCT Pub. Date: Mar. 6, 1997

[30] Foreign Application Priority Data

Aug. 29, 1995 [JP] Japan .................................. 7-220109

[51] Int. Cl.⁶ .................................................. A61K 31/55
[52] U.S. Cl. ............................................................ 514/218
[58] Field of Search ............................................. 514/218

[56] References Cited

FOREIGN PATENT DOCUMENTS

| | | |
|---|---|---|
| 710482 | 5/1996 | European Pat. Off. . |
| 7-145060 | 6/1995 | Japan . |
| 8-59632 | 3/1996 | Japan . |
| 8-73357 | 3/1996 | Japan . |

OTHER PUBLICATIONS

1992 Conn's Current Therapy, edited by Robert E. Rakel, W.B. Saunders Company, 1992.

The Merck Manual, Fourteenth Edition, edited by Robert Barkow, Merck Sharp & Dohme Research Laboratories, 1982.

*Primary Examiner*—Kimberly Jordan
*Attorney, Agent, or Firm*—Oblon, Spivak, McClelland, Maier & Neustadt, P.C.

[57] ABSTRACT

The present invention is directed to a preventive and therapeutic agent for kidney diseases containing as its active component a compound of the following formula (1):

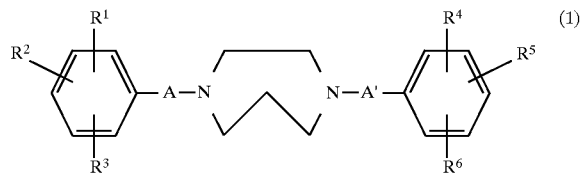

(wherein each of $R^1$, $R^2$, $R^3$, $R^4$, $R^5$, and $R^6$, which may be identical to or different from one another, represents a lower alkoxyl group, and each of A and A', which may be identical to or different from each other, represents a lower alkylene group); an acid addition salt thereof; or a hydrate of the compound of formula (1) or of the acid addition salt thereof. This compound is useful for the prevention and treatment of kidney diseases, as it exhibits excellent preventive and therapeutic effect against acute renal failure, potent inhibitory effect against ischemia-reperfusion disorder in the kidney, and suppressed toxicity.

18 Claims, 2 Drawing Sheets

PREVENTIVE AND THERAPEUTIC AGENT FOR KIDNEY DISEASES

This application is a 371 of PCT/JP96/02341, filed Aug. 22, 1996.

TECHNICAL FIELD

The present invention relates to a preventive and therapeutic agent for kidney diseases and more particularly, to a preventive and therapeutic agent for kidney diseases typified by acute renal failure.

BACKGROUND ART

Renal failure is a state in which renal functions are damaged severely such that internal environment of the living body can no longer be maintained in normal conditions. In particular, acute renal failure—which involves sharp aggravation of renal functions that leads to a loss of homeostasis of body fluid, permitting accumulation of nitrogen metabolites—shows high lethality even with today's advanced dialysis therapy, and is a pathological condition with poor prognosis.

Therapeutic agents for acute renal failure include loop diuretics and osmotic diuretics, which are used in expectation of recovery of renal functions by increasing the flow in kidney tubules so as to wash away casts formed in the tubules and thereby prevent obstruction of the tubules. However, depending on the manner of use, these agents present the risk of inviting hearing disorders and the even more severe adverse side effects of heart failure and pulmonary edema. Therefore, there is demand for development of more effective and safe preventive or therapeutic drugs for acute renal failure.

Accordingly, an object of the present invention is to provide a preventive and therapeutic agent for kidney diseases, particularly, renal failure.

DISCLOSURE OF THE INVENTION

Under the above circumstances, the present inventors conducted careful studies so as to solve the above-mentioned problems, and found that the compounds represented by the following formula (1), their acid addition salts, or hydrates of the formula (1) compounds or of their acid addition salts exhibit potent preventive and therapeutic effects against kidney diseases, particularly renal failure, and moreover, these compounds strongly suppress formation of edemas generated through ischemia-reperfusion, thus leading to completion of the invention.

Accordingly, the present invention provides a preventive and therapeutic agent for kidney diseases comprising as its active component a compound of the following formula (1):

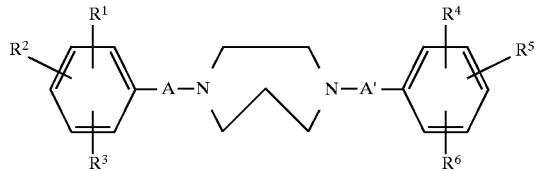

(wherein each of $R^1$, $R^2$, $R^3$, $R^4$, $R^5$, and $R^6$, which may be identical to or different from one another, represents a lower alkoxyl group, and each of A and A', which may be identical to or different from each other, represents a lower alkylene group); an acid addition salt thereof; or a hydrate of the compound of formula (1) or of the acid addition salt thereof.

The present invention also provides a preventive and therapeutic composition for kidney diseases containing a compound of the above formula (1), an acid addition salt thereof, or a hydrate of the compound of formula (1) or of the acid addition salt thereof, in admixture with a pharmaceutically acceptable carrier.

The present invention also provides use of a compound of the above formula (1), an acid addition salt thereof, or a hydrate of the compound of formula (1) or of the acid addition salt thereof, in the preparation of a preventive and therapeutic agent for kidney diseases.

The present invention also provides a method for the prevention and treatment of kidney diseases characterized by administering an effective amount of a compound of the above formula (1), an acid addition salt thereof, or a hydrate of the compound of formula (1) or of the acid addition salt thereof.

BEST MODE FOR CARRYING OUT THE INVENTION

Figure 1:
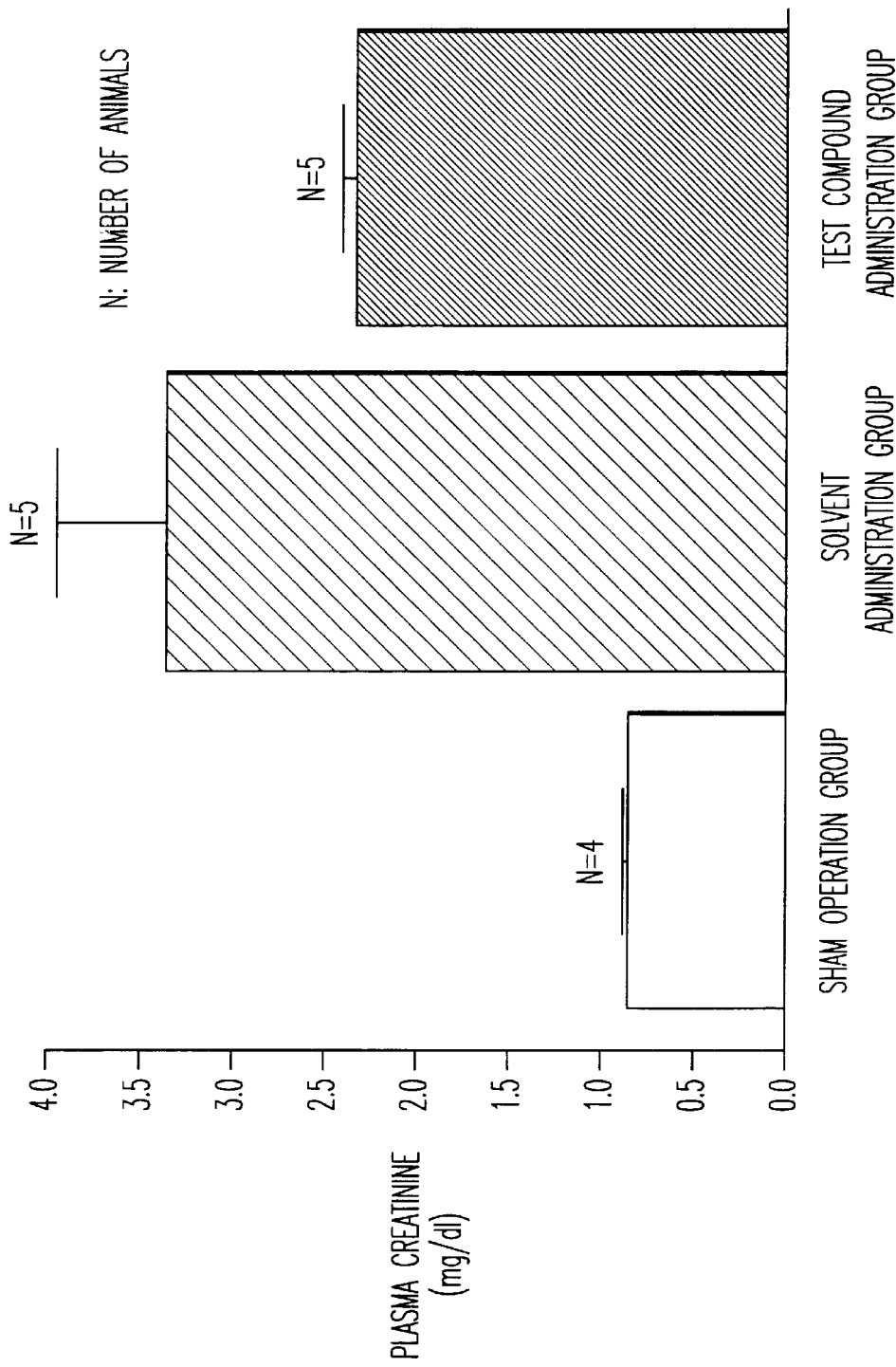
FIG. 1 shows the suppressive effect of the compound against the increase of plasma creatinine in a rat acute renal failure model.

The compounds represented by formula (1) (hereinafter referred to as compounds (1)) which are used in the present invention are known and are described in, for example, Japanese Patent Application Laid-Open (kokai) No. 2144/1991. This publication describes that the compounds are useful as a brain protective agent directed to the amelioration and the prevention of aggravation of cerebral functional disorders accompanied by cerebral hemorrhage, cerebral infarction, subarachnoidal hemorrhage, transient cerebral ischemic attack, and cerebrovascular disorders. However, this publication does not provide any suggestion as to whether or not these compounds are useful as preventive or therapeutic agents for kidney diseases.

In compounds (1), each of the lower alkoxyl groups represented by $R^1$ through $R^6$ preferably has 1 to 6 carbon atoms, with methoxyl, ethoxyl, n-propoxyl, and isopropoxyl being particularly preferred. Groups A and A', which are lower alkylene groups, are preferably C1–C6 linear or branched, with trimethylene, tetramethylene, and pentamethylene being particularly preferred.

Of various members of compounds (1), preferable ones are compounds (1) in which $R^1$ through $R^6$ are methoxyl groups and A and A' are tetramethylene groups. N,N'-bis[4-(3,4,5-trimethoxyphenyl)butyl]homopiperazine is particularly preferred.

Compounds (1) may be prepared in accordance with the methods, particularly method (1), described in Japanese Patent Application Laid-Open (kokai) No. 2144/1991.

In the present invention, in addition to compounds (1), acid addition salts thereof as well as hydrates of compounds (1) or of acid addition salts of compounds (1) may be used. Acid addition salts may be prepared through customary methods. Acids that afford the acid addition salts include inorganic acids such as sulfuric acid, hydrochloric acid, nitric acid, phosphoric acid, and hydrobromic acid; and organic acids such as acetic acid, lactic acid, succinic acid, tartaric acid, malic acid, maleic acid, citric acid, fumaric acid, methanesulfonic acid, and tolunesulfonic acid.

The preventive and therapeutic agent of the present invention comprises as its active component a compound (1), an acid addition salt thereof, or a hydrate of component (1) or of an acid addition salt of compound (1). The active component is used singly or in combination with a pharmaceutically acceptable carrier such as a vehicle, binder, or a diluent, to thereby provide any form of tablets, capsules, granules, powders, injections, or suppositories. These preparations may be manufactured by known methods. For example, when peroral preparations are prepared, compound (1) is formulated in suitable combination with a vehicle such as starch, mannitol, or lactose; a binder such as carboxymethylcellulose-Na or hydroxypropylcellulose; a disintegrant such as crystalline cellulose or carboxymethylcellulose; a lubricant such as talc or magnesium stearate; and a fluidity improver such as light anhydrous silicate.

The dosage of the preventive and therapeutic agent of the present invention varies in accordance with weight, age, sex, condition of the disease, etc. of the patient. Generally, in the case of adults, it is preferred that the preventive and therapeutic agent of the invention be administered to the subject in an amount of 0.1–1,000 mg/day in terms of compound (1), which may be administered as a single dose or 2–3 divided doses. If the agent is administered for extracorporeal circulation, the concentration of compound (1) be adjusted so as to fall within the range between 1 nM and 1 mM.

The preventive and therapeutic agent of the present invention may be administered perorally or systemically to a subject who has been suffering or is considered to be suffering a kidney disease. To a subject who is going to undergo or is undergoing arterial or venous blocking or reperfusion in a surgical operation of the kidney, the agent may be administered perorally, systemically, or by way of addition to extracorporeal circulation of the patient. When renal transplantation is performed, it is preferred that the agent be administered perorally or systemically to the donor of the organ, be added to the preservative of the removed organ, and be administered perorally or systemically to the patient to be transplanted with the organ before and after the operation.

EXAMPLES

The present invention will next be described by way of examples, which should not be construed as limiting the invention thereto.

Preparation Examples

Preparation of N,N'-bis[4-(3,4,5-trimethoxyphenyl)butyl] homopiperazine dihydrochloride:

1-Chloro-4-(3,4,5-trimethoxyphenyl)butane (7.5 g), homopiperazine (1.3 g), potassium carbonate (4.5 g), and potassium iodide (5.3 g) were added to dimethylformamide (4.2 ml), and the resultant mixture was stirred at 100° C. for 1 hour. The reaction mixture was poured into brine, and extracted with ethyl acetate. The ethyl acetate layer was subjected to extraction with dilute HCl. The aqueous layer was washed with ethyl acetate, made basic by use of NaOH, and then extracted with ether. The ether layer was washed with brine and dried, and the solvent was evaporated. The residue was purified by silica gel column chromatography, to thereby obtain 4.7 g of a free base.

The free base was converted through a routine method into a hydrochloric acid salt, which was then recrystallized from methanol-ether, to thereby obtain 3.2 g of the target compound having a melting point of 191°–194° C. (decomposed).

$^1$H-NMR(CDCl$_3$); δ 2.60(4H, br.t, J=8 Hz), 3.82(6H, s), 3.86(12H, s), 6.37(4H, s) IR(KBr); cm$^{-1}$ 1587, 1238, 1122

Example 1

(Suppressive effect against the increase of plasma creatinine in a rat acute renal failure model)

The effect of N,N'-bis[4-(3,4,5-trimethoxyphenyl)butyl] homopiperazine dihydrochloride (hereinafter referred to as a test compound) exerted on a rat suffering acute renal failure was investigated.

Under anesthesia with pentobarbital, the right kidney was removed from each rat. Subsequently, the left side of the back of the rat was incised so as to expose the left renal artery and the left renal vein. The left renal artery was carefully separated so as not to injure the renal sympathetic nerve. The left renal artery was occluded for 30 minutes by use of a microclip. The clip was thereafter removed to thereby establish an acute renal failure model. When 24 hours had passed following removal of the clip, arterial blood was collected in an amount of about 5 ml, which was immediately centrifuged for collection of the supernatant component, i.e., plasma. The plasma creatinine was used as an index of acute renal failure. The amount of creatinine was calculated by use of Jaffe's method. Ten minutes before the clip was set, the test compound was intravenously administered to a rat in an amount of 3 mg/kg body weight.

For comparison, a solvent administration group was provided, in which the physiological saline used as a solvent for the test compound was administered to each rat in the group in the same manner as that used for the test compound. The results obtained from the solvent administration group were compared with those obtained from the test compound administration group. In addition, there was provided a sham operation group, in which only the solvent was administered without use of a clip.

As shown in FIG. 1, the plasma creatinine in the sham operation group was 0.85±0.04 mg/dl, whereas the plasma creatinine in the solvent administration group was 3.35±0.59 mg/dl, showing a significant elevation in plasma creatinine level. On the other hand, plasma creatinine in the test compound administration group was 2.34±0.07 mg/dl, exhibiting suppression in plasma creatinine level as compared with the case of the solvent administration group.

Accordingly, based on the fact that the plasma creatinine—which elevates in the event of acute renal failure—was suppressed by the administration of the test compound, the compound of the present invention was confirmed to have a preventive effect against the onset of acute renal failure.

Example 2

(Suppressive effect against the formation of edema caused by ischemia-reperfusion of the rat kidney)

The effect of N,N'-bis[4-(3,4,5-trimethoxyphenyl)butyl] homopiperazine dihydrochloride (hereinafter referred to as a test compound) exerted on the formation of edema due to ischemia-reperfusion of the rat kidney was investigated.

In accordance with the method described by Peller et al. [J. Clin. Invest., 74, 1156–1164 (1984)], the artery and the vein of the left kidney of each rat were occluded for 30 minutes for imposing a ischemic load. Twenty four hours after the start of reperfusion, the effect of the test compound on the renal disorder was evaluated through use of the water content of the kidney as an index. The water content of the kidney was determined in accordance with the dry weight method described by Stewart-Wallance [Brain, 62, 426–438 (1939)] and Elliott and Jasper [Am. J. Physiol., 157, 122–129 (1949)]. The test compound was intravenously administered twice, i.e., ten minutes before the blockade of the artery and vein of the kidney and immediately after reperfusion was started, in an amount of 3 mg/kg each time. When 24 hours had elapsed following the start of reperfusion, the left kidney was removed, and its wet weight and dry weight were measured. The water content of the kidney was computed in accordance with the following equation.

Water content of kidney (%)=(wet weight of the kidney–dry weight of the kidney)/(wet weight of the kidney)×100

For comparison, a drug non-administration group (Control group) in which the solvent used for the test compound (physiological saline) was administered to each rat in the group was provided, as well as a sham operation group (Sham group) in which the renal artery and vein were separated and the ischemic load was not applied. The results from these two groups were compared with the results from the test compound administration group.

Figure 2:
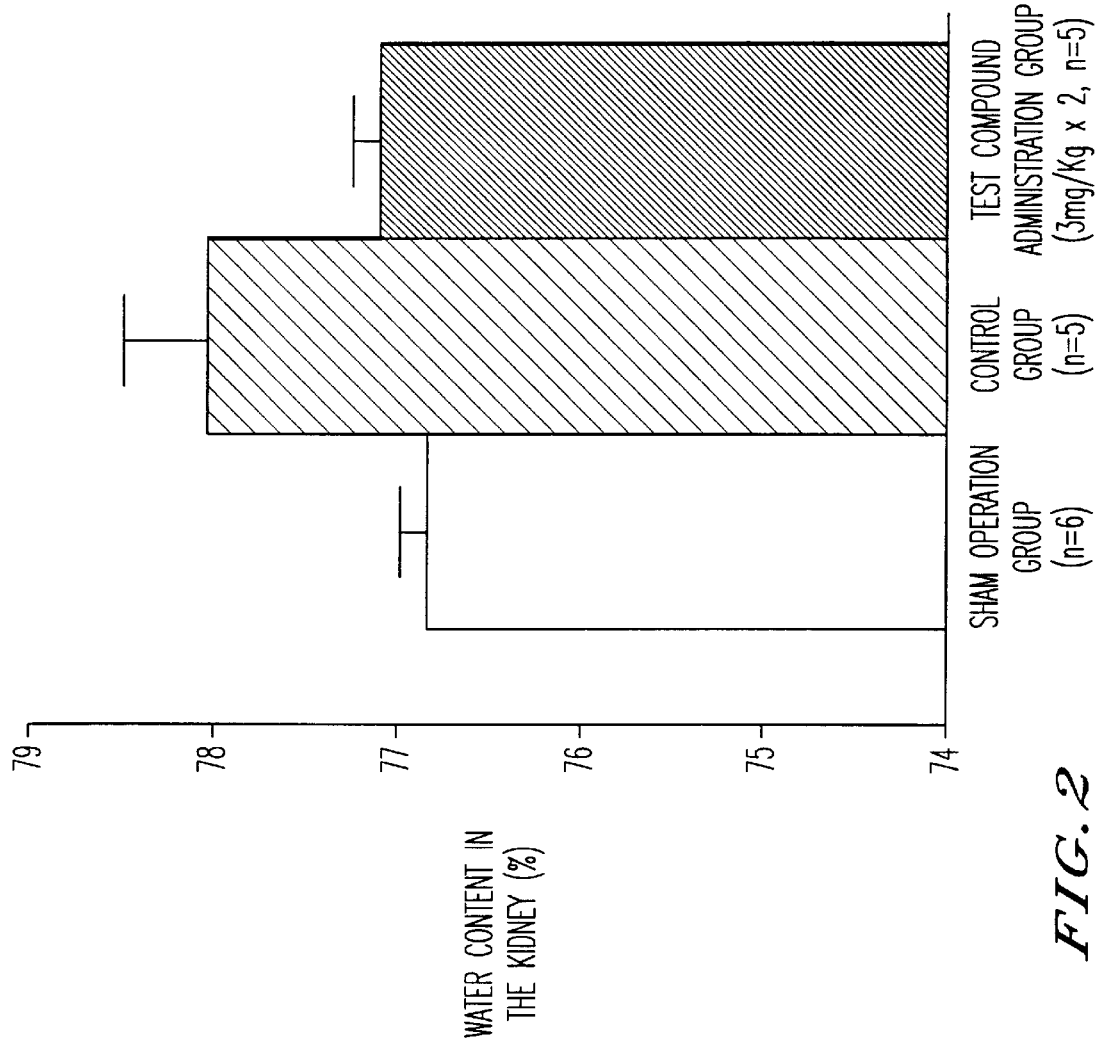
FIG. 2 shows the suppressive effect of the compound against the formation of edemas caused by ischemia-reperfusion of the rat kidney.

As shown in FIG. 2, the water content of the kidney in the Sham group was 76.82%, whereas that in the Control group whose members underwent an ischemia-reperfusion treatment was 78.04%, showing a significant elevation of 1.22%. On the other hand, the water content of the kidney in the test compound administration group was 77.10%, exhibiting a suppressed increase in water content. When the percent increase of the water content in the Control group with respect to the water content in the Sham group is regarded as 100%, the test compound exhibited a 77% suppression in increase of the water content attributed to ischemia-reperfusion.

Moreover, although no results are shown herein, the test compound remarkably inhibited the increase of the water content attributed to ischemia-reperfusion with only a single administration of the compound immediately after reperfusion.

Based on the above results, the test compound was confirmed to have a potent inhibitory action against formation of edema due to ischemia-reperfusion of the rat kidney.

Example 3

(Acute toxicity test)

Groups of Slc:Wistar male rats, each group consisting of 5 rats (about 10 weeks old), were used. A test compound suspended in 5% gum arabic was perorally administered to each rat at a dose of 300 mg/kg or 1,000 mg/kg. The behavior of each rat was observed at 0.5, 1, 2, and 4 hours after the administration. Thereafter, the animals were fed and observed for 3 days.

As a result, the test compound did not induce any abnormal behavior or death of rats in either case of 300 mg/kg or 1,000 mg/kg peroral administration.

Example 4 (Capsules)

N,N'-bis[4-(3,4,5-trimethoxyphenyl)butyl]homopiperazine dihydrochloride 30 mg
Microcrystalline cellulose 30 mg
Lactose 57 mg
Magnesium stearate 3 mg
Total amount 120 mg The above ingredients were mixed through use of a customary method and put in gelatin capsules, to thereby obtain a capsule agent.

Example 5 (Tablets)

N,N'-bis[4-(3,4,5-trimethoxyphenyl)butyl]homopiperazine dihydrochloride 30 mg
Starch 44 mg
Starch (for paste) 5.6 mg
Magnesium stearate 0.4 mg
Carboxymethylcellulose-Ca 20 mg
Total amount 100 mg The above ingredients were mixed through use of a customary method, to thereby obtain tablets.

Example 6 (Injection)

N,N'-bis[4-(3,4,5-trimethoxyphenyl)butyl]homopiperazine dihydrochloride (100 mg) and sodium chloride (900 mg) were dissolved in distilled water for injection use (ca. 80 ml). Subsequently, to the resultant solution was added distilled water for injection use so as to make the total amount 100 ml. The resultant solution was aseptically filtered, dispensed into 10 light-shielded ampules, to thereby obtain sterile injections.

Industrial Applicability

The preventive and therapeutic agents of the present invention exhibit excellent preventive and therapeutic effect against acute renal failure, potent inhibitory effect against ischemia-reperfusion disorder in the kidney, and suppressed toxicity. Therefore, they are useful for the prevention and treatment of kidney diseases.

We claim:

1. A preventive and therapeutic agent for a kidney disease selected from the group consisting of renal failure and edema, wherein the agent comprises as its active component a compound of the following formula (I):

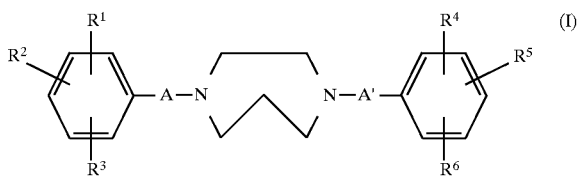

(wherein each of $R^1$, $R^2$, $R^3$, $R^4$, $R^5$, and $R^6$, which may be identical to or different from one another, represents a lower alkoxyl group, and each A and A', which may be identical to or different from each other, represents a lower alkylene group); an acid addition salt thereof; or a hydrate of the compound of formula (I) or of the acid addition salt thereof.

2. The preventive and therapeutic agent as claimed in claim 1 wherein the kidney disease is renal failure.

3. A preventive and therapeutic composition for a kidney disease selected from the group consisting of renal failure and edema, wherein the composition contains a compound of formula (I) as defined in claim 1, an acid addition salt thereof, or a hydrate of the compound of formula (I) or of the acid addition salt thereof, in admixture with a pharmaceutically acceptable carrier.

4. The preventive and therapeutic composition as claimed in claim 3, wherein the kidney disease is renal failure.

5. The preventive and therapeutic composition as claimed in claim 3, wherein the kidney disease is caused by ischemia-reperfusion.

6. A method for the prevention and treatment of a kidney disease selected from the group consisting of renal failure and edema, characterized by administering an effective amount of a compound as defined in claim 1, an acid addition salt thereof, or a hydrate of the compound as defined in claim 1 or of the acid addition salt thereof to a patient in need thereof.

7. The preventive and therapeutic method as claimed in claim 6, wherein the kidney disease is renal failure.

8. The preventive and therapeutic method as claimed in claim 6, wherein the kidney disease is caused by ischemia-reperfusion.

9. The preventive and therapeutic agent as claimed in claim 1, wherein the kidney disease is caused by ischemia-reperfusion.

10. A preventive and therapeutic agent for a kidney disease selected from the group consisting of renal failure and edema, wherein the agent comprises as its active component N,N'-bis[4-(3,4,5-trimethoxyphenyl)butyl]homopiperazine, an acid addition salt thereof, or a hydrate of N,N'-bis[4-(3,4,5-trimethoxyphenyl)butyl]homopiperazine or of the acid addition salt thereof.

11. The preventive and therapeutic agent as claimed in claim 10, wherein the kidney disease is renal failure.

12. The preventive and therapeutic agent as claimed in claim 10, wherein the kidney disease is caused by ischemia-reperfusion.

13. A preventive and therapeutic composition for a kidney disease selected from the group consisting of renal failure and edema, wherein the composition contains N,N'-bis[4-(3,4,5-trimethoxyphenyl)butyl]homopiperazine, an acid addition salt thereof, or a hydrate of N,N'-bis[4-(3,4,5-trimethoxyphenyl)butyl]homopiperazine or of the acid addition salt thereof, in admixture with a pharmaceutically acceptable carrier.

14. The preventive and therapeutic composition as claimed in claim 13, wherein the kidney disease is renal failure.

15. The preventive and therapeutic composition as claimed in claim 13, wherein the kidney disease is caused by ischemia-reperfusion.

16. A method for the prevention and treatment of a kidney disease selected from the group consisting of renal failure and edema, characterized by administering an effective amount of N,N'-bis[4-(3,4,5-trimethoxyphenyl)butyl]homopiperazine, an acid addition salt thereof, or a hydrate of N,N'-bis[4-(3,4,5-trimethoxyphenyl)butyl]homopiperazine or of the acid addition salt thereof to a patient in need thereof.

17. The preventive and therapeutic method as claimed in claim 16, wherein the kidney disease is renal failure.

18. The preventive and therapeutic method as claimed in claim 16, wherein the kidney disease is caused by ischemia-reperfusion.

* * * * *